US00PP32050P2

(12) United States Plant Patent
Trees

(10) Patent No.: US PP32,050 P2
(45) Date of Patent: Aug. 11, 2020

(54) ***LANTANA* PLANT NAMED 'BALUCPEA20'**

(50) Latin Name: *Lantana camara*
Varietal Denomination: Balucpea20

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/602,137

(22) Filed: Aug. 12, 2019

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./227
See application file for complete search history.

*Primary Examiner* — Susan McCormick Ewoldt
(74) *Attorney, Agent, or Firm* — Audrey Charles

(57) ABSTRACT

A new and distinct cultivar of *Lantana* plant named 'Balucpea20', characterized by its yellow, orange, and reddish-purple multicolored inflorescences, dark green-colored foliage, and moderately vigorous, upright-mounded growth habit, is disclosed.

1 Drawing Sheet

Latin name of genus and species of plant claimed: *Lantana camara.*
Variety denomination: 'Balucpea20'.

BACKGROUND OF THE INVENTION

The present invention relates to a new and distinct cultivar of *Lantana* plant botanically known as *Lantana camara* and hereinafter referred to by the cultivar name 'Balucpea20'.

The new cultivar originated in a controlled breeding program in Guadalupe, Calif. during September 2013. The objective of the breeding program was the development of *Lantana* cultivars with continuous flowering and a moderately vigorous, upright-mounded growth habit.

The new *Lantana* cultivar is the result of cross-pollination. The female (seed) parent of the new cultivar is the proprietary *Lantana camara* breeding selection coded 9087, not patented, characterized by its dark red-colored inflorescences, medium green-colored foliage, low growth vigor and compact-mounded growth habit. The male (pollen) parent of the new cultivar is BANDANA Peach 'LANZ0002', U.S. Plant Pat. No. 23,317, characterized by its yellow, orange, and light red multicolored flowers, medium green-colored foliage, and moderately vigorous, relatively compact and mounding growth habit. The new cultivar was discovered and selected as a single flowering plant within the progeny of the above stated cross-pollination during September 2014 in a controlled environment in Guadalupe, Calif.

Asexual reproduction of the new cultivar by terminal stem cuttings since September 2014 in Guadalupe, Calif. and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balucpea20' as a new and distinct cultivar of *Lantana* plant:

1. Yellow, orange, and reddish-purple multicolored inflorescences;
2. Dark green-colored foliage; and
3. Moderately vigorous, upright-mounded growth habit.

Plants of the new cultivar differ from plants of the female parent primarily in inflorescence color, darker green foliage color, and a more vigorous growth habit. Plants of the new cultivar differ from plants of the male parent primarily in being shorter and narrower with a less rounded growth habit.

Of the many commercially available *Lantana* cultivars, the most similar in comparison to the new cultivar is Little Lucky Peach Glow 'Balluceagl', U.S. Plant Pat. No. 24,554. However, in side-by-side comparisons, plants of the new cultivar differ from plants of 'Balluceagl' in at least the following characteristics:

1. Plants of the new cultivar have darker orange-colored inflorescences than plants of 'Balluceagl'; and
2. Plants of the new cultivar are taller and wider than plants of 'Balluceagl'.

The new cultivar can also be compared to Bloomify Mango 'Baloomang' U.S. Plant patent application Ser. No. 16/602,134. However, in side-by-side comparison, plants of the new cultivar differ from plants of 'Baloomang' in at least the following characteristics:

1. Plants of the new cultivar are shorter and narrower than plants of 'Baloomang';
2. Plants of the new cultivar have flower buds with more yellow coloration than plants of 'Baloomang'; and
3. Plants of the new cultivar have smaller leaves than plants of 'Baloomang'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balucpea20'. The plants were approximately 5 months old and grown in 4.5-inch pots for approximately 15 weeks in a greenhouse in West Chicago, Ill.

DETAILED BOTANICAL DESCRIPTION

Figure 1:
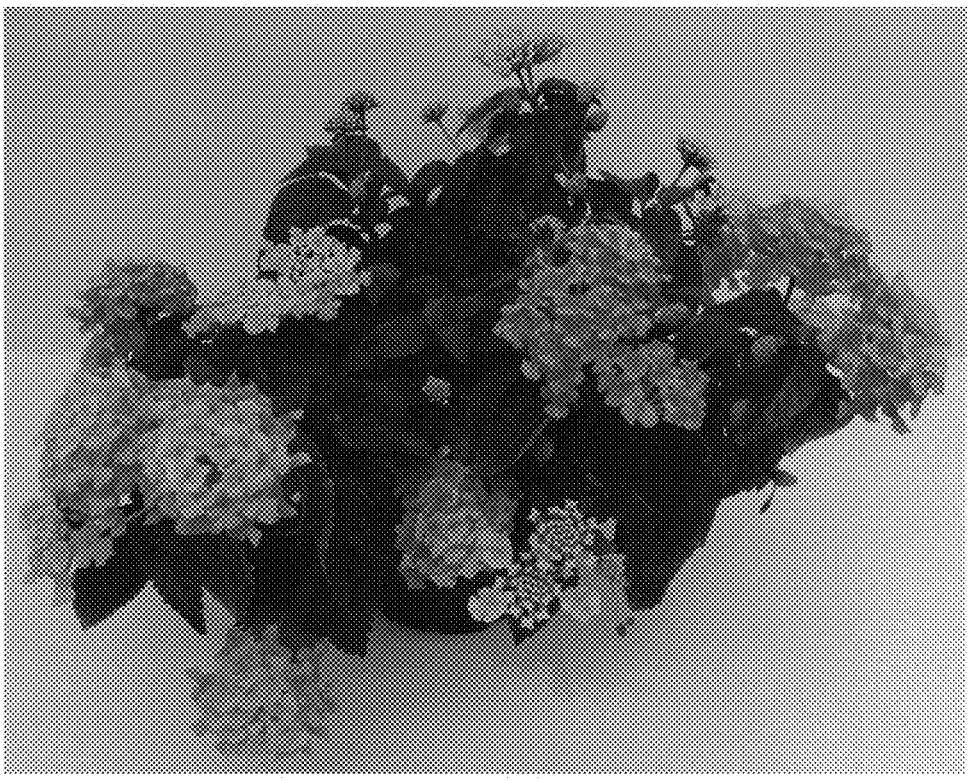
FIG. 1 illustrates a side view of the overall growth and flowering habit of 'Balucpea20'.
Figure 2:
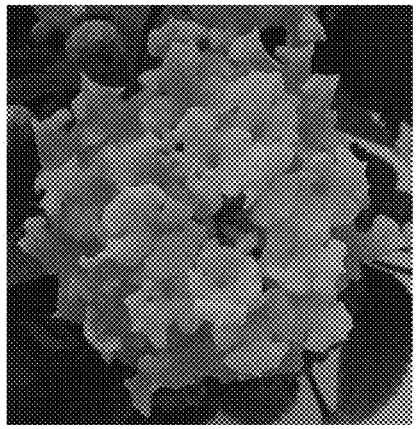
FIG. 2 illustrates a close-up view of an individual inflorescence of 'Balucpea20'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2019 under natural light conditions in West Chicago, Ill.

The following descriptions and measurements describe approximately 5-month old plants produced from cuttings from stock plants and grown in a glass-covered greenhouse under conditions comparable to those used in commercial practice. The plants were grown in West Chicago, Ill. in 4.5-inch pots for approximately 15 weeks utilizing a soilless growth medium. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Lantana camara* 'Balucpea20'.

Parentage:

*Female parent*.—Proprietary *Lantana camara* breeding selection coded 9087, not patented.

*Male parent*.—BANDANA Peach, U.S. Plant Pat. No. 23,317.

Propagation:

*Type cutting*.—Terminal stem.

*Time to initiate roots*.—Approximately 7 to 11 days.

*Time to produce a rooted cutting*.—Approximately 24 to 35 days.

*Root description*.—Fibrous.

*Rooting habit*.—Freely branching.

Plant description:

*Commercial crop time*.—Approximately 6 to 7 weeks from a rooted cutting to finish in a 10 cm pot.

*Growth habit and general appearance*.—Moderately vigorous, upright-mounded.

*Size*.—Height from soil level to top of plant plane: Approximately 15.0 cm. Width: Approximately 26.0 cm.

*Branching habit*.—Freely branching, pinching enhances branching. Quantity of lateral branches per plant: Approximately 5.

*Branch*.—Shape: Square in cross section. Strength: Strong, becomes woody with age. Length: Approximately 10.5 cm. Diameter: Approximately 3.0 mm. Length of central internode: Approximately 1.6 cm. Texture: Densely pubescent with a mixture of glandular and nonglandular hairs. Gland color: Colorless, transparent. Color of young stem: 144A. Color of mature stem: 146B becoming woody N199A with age.

Foliage description:

*General description*.—Quantity of leaves per lateral branch: Approximately 12. Fragrance: Strong, spicy. Form: Simple. Arrangement: Opposite.

*Leaves*.—Aspect: Perpendicular to obtuse angle to stem. Shape: Ovate. Margin: Serrate. Apex: Acute. Base: Obtuse. Venation pattern: Pinnate. Length of mature leaf: Approximately 6.0 cm. Width of mature leaf: Approximately 3.8 cm. Texture of upper surface: Scabrous. Texture of lower surface: Scabrous and glandular pubescent along venation. Gland color: Colorless, transparent. Color of upper surface of young foliage: 137A with venation of 146B to indistinguishable. Color of lower surface of young and mature foliage: Closest to 138B with venation of 146C. Color of upper surface of mature foliage: Closest to NN137A with 139A, venation of 146B to indistinguishable.

*Petiole*.—Length: Approximately 1.3 cm. Diameter: Approximately 2.0 mm. Texture: Scabrous and glandular pubescent. Gland color: Colorless, transparent. Color: 146B.

Flowering description:

*Flowering habit*.—'Balucpea20' is freely flowering under outdoor growing conditions with substantially continuous blooming from spring through autumn and year-round in greenhouse environment.

*Lastingness of individual inflorescence on the plant*.—Approximately 10 to 12 days from first color of outer buds to dropping of last flower.

Inflorescence description:

*General description*.—Type: Hemispherical head, axillary or terminal. Quantity per plant: Approximately 14. Fragrance: Strong, spicy. Aspect: Facing upward or outward. Height: Approximately 2.8 cm. Width: Approximately 4.5 cm. Quantity of fully open flowers per inflorescence: Approximately 30.

*Peduncle*.—Strength: Strong. Shape: Square in cross section. Aspect: Acute angle to stem. Length: Approximately 3.0 cm. Diameter: Approximately 2.0 mm. Texture: Scabrous and glandular pubescent. Gland color: Colorless, transparent. Color: 146B.

Flower description:

*General description*.—Type: Salverform.

*Bud*.—Rate of opening: Generally takes 1 to 2 days for bud to progress from first color to fully open flower. Buds open in progression from the margin to the center of the inflorescence. Quantity of unopened inflorescences per plant: Approximately 8.

*Bud just before opening*.—Shape: Elongated, rectangular at apex. Length: Approximately 1.1 cm. Diameter: Approximately 4.0 mm. Color: 16C.

*Corolla*.—Depth: Approximately 2.2 cm. Diameter: Approximately 1.3 cm.

*Petals*.—Quantity: 4, non-imbricate, non-symmetrical petals. Petals are fused at base forming a corolla tube. Shape: Obovate. Appearance: Dull. Aspect: Flat to cupped. Margin: Entire to erose, ruffled. Apex: Obtuse. Length of upper petal from throat: Approximately 6.0 mm. Width of upper petal: Approximately 9.0 mm. Length of lateral petals from throat: Approximately 5.0 mm. Width of lateral petals: Approximately 6.0 mm. Length of lower petal from throat: Approximately 7.0 mm. Width of lower petal: Approximately 8.0 mm. Texture of upper surface: Glabrous. Texture of lower surface: Densely pubescent. Color of upper surface when first open: 12A to 12B with 15A at tube opening and margins of 12D. Color of lower surface when first open: 4D. Color of upper surface when fully open: N25C with N25A at tube opening and margins of N77D. Color of lower surface when fully open: 17D tinted with N77D on margins.

*Corolla tube*.—Length: Approximately 1.3 cm. Diameter at tube opening: Approximately 1.0 mm. Diameter at base: Approximately 1.0 mm. Texture of inner surface: Densely pubescent. Texture of outer surface: Densely pubescent with a mixture of glandular and nonglandular hairs at tube opening transitioning to glabrous at base. Pubescence color: Colorless and 53D. Color of inner surface: 15A. Color of outer surface: 151D with an overlay of 53D, overlay becomes heavier with age.

*Calyx*.—Shape: Tubular with two broadly acute tips. Length: Approximately 3.0 mm. Diameter at tip: Approximately 1.5 mm. Diameter at base: Approximately 1.5 mm. Texture of inner surface: Glabrous. Texture of outer surface: Densely pubescent with a mixture of glandular and nonglandular hairs. Gland color: Colorless, transparent. Color of inner and outer surfaces: 145D.

*Bracts*.—Quantity per flower: 1 per flower. Shape: Lanceolate. Length: Approximately 7.0 mm. Width: Approximately 2.0 mm. Texture of upper surface: Sparsely pubescent. Texture of lower surface: Densely pubescent. Color of upper surface: 137A with 146B at base. Color of lower surface: 137B with 146B at base.

*Reproductive organs*.—Androecium: Stamen quantity: 4, adnate to corolla tube. Stamen length: Approximately 2.0 mm. Anther shape: Bilobed, ovoid. Anther length: Approximately 1 mm. Anther color: 13B. Pollen amount: None observed. Gynoecium: Pistil quantity: 1 per flower. Pistil length: Approximately 4.0 mm. Stigma shape: Oval. Stigma length: Less than 1 mm. Stigma color: 144B, translucent. Style length: Approximately 3.0 mm. Style color: 145D, translucent. Ovary diameter: Approximately 1.0 mm. Ovary color: 144B.

Seed and fruit production: Neither seed nor fruit production has been observed.

Disease and pest resistance: Resistance to pathogens and pests common to *Lantana* has not been observed.

What is claimed is:

1. A new and distinct cultivar of *Lantana* plant named 'Balucpea20', substantially as herein illustrated and described.

* * * * *